United States Patent [19]

Cohen

[11] 4,089,966
[45] May 16, 1978

[54] 5-N-(3-AMINO-2-HYDROXY-PROPYL)-AMINO-1,2,4-OXADIAZOLE DERIVATIVES, PROCESSES FOR THEIR PREPARATION AND APPLICATIONS THEREOF

[75] Inventor: Claude Cohen, Versailles, France

[73] Assignee: Aron Sarl, Suresnes, France

[21] Appl. No.: 696,722

[22] Filed: Jun. 16, 1976

[30] Foreign Application Priority Data

Jun. 23, 1975 United Kingdom ............ 26590/75

[51] Int. Cl.² .................... C07D 271/06; A61K 31/42
[52] U.S. Cl. ................................. 424/272; 260/296 R; 260/307 G; 424/250; 424/263; 544/364; 544/367
[58] Field of Search ..................... 260/307 G; 424/272

[56] References Cited

U.S. PATENT DOCUMENTS

| 3,338,899 | 8/1967 | Aron-Samuel et al. ............ 260/268 |
| 3,538,087 | 11/1970 | Troxler et al. ....................... 260/240 |
| 3,574,222 | 4/1971 | Eloy et al. ............................. 260/296 |

*Primary Examiner*—Raymond V. Rush
*Attorney, Agent, or Firm*—Young & Thompson

[57] ABSTRACT

This invention relates to compounds having the formula:

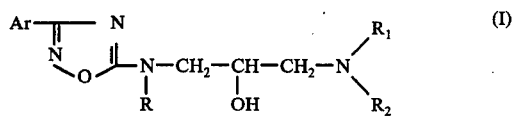

(I)

in which:
Ar represents a phenyl, pyridyl, isoxazolyl, oxazolyl or pyrazolyl radical which may be mono- or polysubstituted with halogen atoms, hydroxy radicals, $C_{1-4}$ alkyl radicals or $C_{1-4}$ alkoxy radicals, R represents a hydrogen atom, a $C_{1-4}$ alkyl radical, a $C_{2-4}$ alkenyl radical, a $C_{2-4}$ alkynyl radical, a hydroxy-$C_{1-4}$alkyl radical, a mono- or di-$C_{1-4}$alkyl-amino-$C_{1-4}$alkyl radical or a phenyl radical, $R_1$ and $R_2$, when taken separately, represent each a hydrogen atom or a $C_{1-4}$ alkyl radical or, when taken together with the nitrogen atom to which they are attached, form a saturated or unsaturated 5- or 6-membered heterocyclic radical which may optionally contain, as second heteroatom, an oxygen or nitrogen atom and which may carry a $C_{1-4}$ alkyl radical; and their therapeutically acceptable acid addition salts. Said compounds are useful for the treatment or the prevention of disorders of the cardiac rhythm in Man.

19 Claims, No Drawings

5-N-(3-AMINO-2-HYDROXY-PROPYL)-AMINO-1,2,4-OXADIAZOLE DERIVATIVES, PROCESSES FOR THEIR PREPARATION AND APPLICATIONS THEREOF

This invention relates to new 5-amino-1,2,4-oxadiazole derivatives, processes for their preparation and applications thereof.

A number of 5-amino-1,2,4-oxadiazole derivatives are already known. Thus, 3-phenyl-5-amino-1,2,4-oxadiazole derivatives are disclosed in French Pat. Nos. 2023 M, 1,575,544; 1,559,629 and 1,506,232. The first two patents disclose the vasodilator and anesthetic properties of the compounds described. French Pat. No. 1,559,629 discloses essentially the analgesic and anti-inflammatory properties of the compounds. The compounds of French Pat. No. 1,506,232 are described essentially as curing agents for epoxy resins.

This invention relates to new 5-amino-1,2,4-oxadiazole derivatives having the formula:

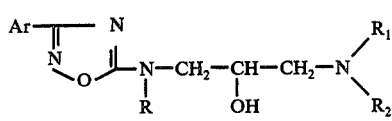

in which:
- Ar represents a phenyl, pyridyl, isoxazolyl, oxazolyl or pyrazolyl radical, which radicals may be mono- or poly-substituted with halogen atoms, hydroxy radicals, $C_{1-4}$ alkyl radicals or $C_{1-4}$ alkoxy radicals,
- R represents a hydrogen atom, a $C_{1-4}$ alkyl radical, a $C_{2-4}$ alkenyl radical, a $C_{2-4}$ alkynyl radical, a hydroxy-$C_{1-4}$ alkyl radical, a mono- or di-$C_{1-4}$ alkylamino-$C_{1-4}$ alkyl radical or a phenyl radical,
- $R_1$ and $R_2$, when taken separately, represent each a hydrogen atom or a $C_{1-4}$ alkyl radical or, when taken together with the nitrogen atom to which they are attached, form a saturated or unsaturated 5- or 6-membered heterocyclic radical which may optionally contain, as second heteroatom, an oxygen or nitrogen atom and which may carry a $C_{1-4}$ alkyl radical, and their therapeutically acceptable acid addition salts.

An advantageous class of compounds of the formula (I) is that in which:
- Ar represents a phenyl or pyridyl radical, which radicals may be substituted with a halogen atom,
- R represents a hydrogen atom, A $C_{1-4}$ alkyl radical or a $C_{2-4}$ alkenyl radical,
- $R_1$ and $R_2$, when taken separately, represent each a hydrogen atom or a $C_{1-4}$ alkyl radical or, when taken together, form a N($C_{1-4}$ alkyl)piperazino radical.

The acid addition salts may typically be those formed with hydrochloric, sulfuric, phosphoric, methanesulfonic, maleic, succinic, pamoic, acetic, fumaric, lactic, aspartic and citric acids.

It should be noted that the invention encompasses both the racemic and the enantiomorphic forms of the compounds of the formula (I).

The compounds of the formula (I) may be prepared by reacting
1. a propanol diamine of the formula:

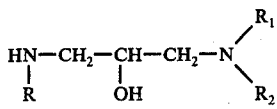

with:
a. a chlorinated compound of the formula:

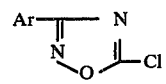

b. a trichloromethyl compound of the formula:

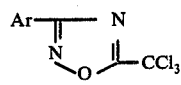

or
c. a compound of the formula:

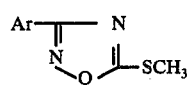

or by reacting
2. a compound of the formula:

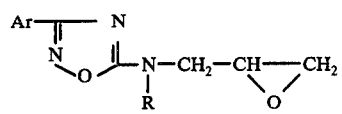

with an amine of the formula

or by reacting
3. a compound of the formula:

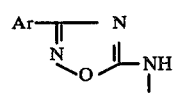

with an epoxypropylamine of the formula:

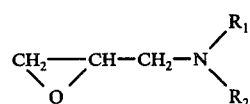

Ar, R, $R_1$ and $R_2$, in formulae (II)–(IX) having the meanings given for formula (I).

The reaction of a propanol diamine of the formula (II) with a compound of the formula (III) may advantageously be effected in heterogeneous water/methylene chloride medium at or about room temperature. Reaction time may vary from a few minutes to several hours.

The reaction of a propanol diamine of the formula (II) with a compound of the formula (IV) may advantageously be effected within a polar solvent such as acetonitrile or within an alcohol, at a temperature comprised between room temperature and the refluxing temperature. Reaction time may vary from a few minutes to several hours.

The reaction of a propanol diamine of the formula (II) with a compound of the formula (V) may advantageously be effected with or without solvent, with or without pressure, at moderate or relatively high temperature.

The reaction of a compound of the formula (VI) with an amine of the formula (VII) may advantageously be effected with or without solvent, at room or moderate temperature. It is substantially complete within a few hours.

The reaction of a compound of the formula (VIII) with an epoxy propylamine of the formula (IX) may advantageously be conducted within aprotic or aromatic solvents at moderate temperature. The reaction is complete within a few hours.

The following non-limiting Examples illustrate the preparation of compounds of the formula (I).

EXAMPLE 1 (Process 1a)

In a three-necked 2 liter flask are added, with stirring, 500 ml water and 80 g 1-diethylamino-2-hydroxy-3-methylamino-propane followed by 50 ml caustic soda Lye ($d = 1.33$). A solution of 90 g 5-chloro-3-phenyl-1,2,4-oxadiazole in 500 ml methylene chloride is then added thereto, over a period of time of 10 minutes. The temperature rises sharply. The mixture is stirred during a further 2 hours. The organic phase is decanted, the aqueous phase is extracted with 250 ml methylene chloride, the organic phases are combined and evaporated to dryness. The resulting yellow oil is dissolved in 520 ml isopropanol. 26.6 g fumaric acid is then added and the resulting material is heated to the refluxing temperature. Crystallization begins on cooling. The solid material is recrystallized from 500 ml isopropanol, to give 149 g (Yield: 82%) 5-N-(3-diethylamino-2-hydroxy-propyl)-N-methylamino-3-phenyl-1,2,4-oxadiazole fumarate hydrate. M.p.(cap.) = 141°–142° C.

The product obtained under such conditions corresponds to the conversion to the salt form of two molecules of 5-N-(3-diethylamino-2-hydroxy-propyl)-N-methylamino-3-phenyl-1,2,4-oxadiazole with one molecule of fumaric acid, with one molecule water of hydration.

The characteristics of the compound obtained in Example 1 are tabulated in the following Table, together with those of other compounds prepared in an analogous manner (Examples 2–12).

In this Table, the fumarates correspond to the salt obtained from 2 molecules of base and 1 molecule fumaric acid.

TABLE I

| Example | Ar | R | $-N\begin{matrix}R_1\\R_2\end{matrix}$ | Salt | M.p.(cap.)* (° C) |
|---|---|---|---|---|---|
| 1 | $C_6H_5$ | $CH_3$ | $-N(C_2H_5)_2$ | fumarate hydrate | 141–142 |
| 2 | $C_6H_5$ | H | $-N(C_2H_5)_2$ | HCl | 103–105 |
| 3 | $3Cl-C_6H_4$ | H | $-N(C_2H_5)_2$ | fumarate | 110–112 |
| 4 | $4F-C_6H_4$ | H | $-N(C_2H_5)_2$ | fumarate | 173–174 |
| 5 | $C_6H_5$ | $C_2H_5$ | $-N(C_2H_5)_2$ | fumarate | 114–116 |
| 6 | $C_6H_5$ | $CH(CH_3)_2$ | $-N(C_2H_5)_2$ | fumarate hydrate | 118–119 |
| 7 | $C_6H_5$ | $nC_3H_7$ | $-N(C_2H_5)_2$ | fumarate hydrate | 104–106 |
| 8 | $C_6H_5$ | $CH_2CH=CH_2$ | $-N(C_2H_5)_2$ | fumarate | 105–106 |
| 9 | $C_6H_5$ | $CH_3$ | $-N(C_3H_7)_2$ | fumarate hydrate | 78 |

TABLE I-continued

| Example | Ar | R | $-N\begin{smallmatrix}R_1\\R_2\end{smallmatrix}$ | Salt | M.p.(cap.)* (° C) |
|---|---|---|---|---|---|
| 10 | $C_6H_5$ | H | $-N\underset{\phantom{x}}{\diagdown}N-CH_3$ | fumarate | 168 (dec.); Kofler block: 208 |
| 11 | (pyridyl) | $CH_3$ | $-N\begin{smallmatrix}C_2H_5\\C_2H_5\end{smallmatrix}$ | 2 HCl | 197–199 |
| 12 | $C_6H_5$ | $C_2H_5$ | $-NH-C_2H_5$ | fumarate | 157–158 |

*Melting point in capillary tube, after introduction 10° C below the melting point and heating at a rate of 2° C/minute.

EXAMPLE 13 (Process 1b)

To a solution of 28.1 g 3-p-fluorophenyl-5-trichloromethyl-1,2,4-oxadiazole in 100 ml methanol is added a solution of 14.6 g 1-diethylamino-3-amino-2-propanol in 50 ml methanol. The temperature rises to 35° C. The resulting mixture is then refluxed during 2 hours, after which the methanol is removed in vacuo.

The residue is taken up into 100 ml water, made acidic and extracted with ether; the aqueous layer is separated, made alkaline and extracted with methylene chloride. The methylene chloride extract is then dried and concentrated in vacuo, to give 23.5 g of base which is then dissolved in 120 ml isopropanol and treated with 4.5 g fumaric acid. Recrystallization from isopropanol gives 18.7 g 5-(3-diethylamino-2-hydroxy-propyl)-amino-3-(4-fluorophenyl)-1,2,4-oxadiazole fumarate, M.p. (cap.): 173°–174° C.

EXAMPLE 14 (Process 1c)

3-Phenyl-5-methylthio-1,2,4-oxadiazole (9.6 g) and 1-diethylamino-3-propylamino-2-propanol (18.8 g) are heated during 2 hours in a sealed tube, at 100° C. The contents of the tube are allowed to cool and are then poured into 200 ml water, after which the organic layer is decanted and the aqueous phase is extracted with methylene chloride. The combined organic phases are washed with water and dried over sodium sulfate.

The methylene chloride and the residual amine are then removed under a vacuum of 1 mm Hg, to give 6 g of base which is treated with 1 g fumaric acid and 0.5 ml water in 50 ml isopropanol. Recrystallization from isopropanol gives 3.2 g 5-[N-(3-diethylamino-2-hydroxy-propyl)-N-propyl]amino-3-phenyl-1,2,4-oxadiazole fumarate hydrate. M.p. (cap.)= 104°–106° C.

EXAMPLE 15 (Process 2)

5-[N(2,3-epoxy-propyl)-N-methyl]-amino-3-phenyl-1,2,4-oxidiazole (23.1 g) in pure dipropylamine (50 ml) are refluxed during 3 hours.

After cooling the mixture, the excess dipropylamine is removed in vacuo, to give 22 g of base which is then treated with 3.8 g fumaric acid and 1 ml water in 100 ml ethanol. Recrystallization from ethanol gives 15.5 g 5-N-(3-dipropylamino-2-hydroxy-propyl)-N-methylamino-3-phenyl-1,2,4-oxadiazole fumarate hydrate. M.p. (cap.): 78° C.

Example 15 (Process 3)

3-(3-Chloro-phenyl)-5-amino-1,2,4-oxadiazole (19.5 g) and sodamide (3.9 g) are heated during 5 hours in 200 ml toluene. The reaction mixture is then cooled to 65°–70° C and a solution of 1-diethylamino-2,3-epoxy-propane (12.9 g) in toluene (50 ml) is added thereto. The resulting mixture is refluxed during 3 hours.

After cooling, the material is made acidic with 100 ml 2N hydrochloric acid. The acidic aqueous phase is decanted, made alkaline and extracted with 2 × 100 ml methylene chloride. The methylene chloride extracts are then dried and the methylene chloride is removed in vacuo, to give 12 g of base which is treated with 2 g fumaric acid in 80 ml ethanol. Recrystallization from ethanol gives 6.8 g 5-(3-diethylamino-2-hydroxy-propyl)-amino-3-(3-chloro-phenyl)-1,2,4-oxadiazole fumarate. M.p. (cap.): 110°–112° C.

The compounds of the formula (I) were found to possess valuable pharmacological properties. In particular, they reduce or abolish auricular and ventricular arrhythmia and are therapeutically useful for the treatment of arrhythmia.

Results of toxicological and pharmacological investigations that provide evidence of such properties are given below.

Acute Toxicity

The acute toxicity of the various compounds is summarized in the Table below. Each value represents the LD 50% expressed as mg/kg, according to the semilogarithmic technique disclosed by Lichfield and Wilcoxon.

TABLE II

| Compound of Example n° | | 1 | 2 | 4 | 5 | 7 | 9 | 10 | 11 |
|---|---|---|---|---|---|---|---|---|---|
| $LD_{50}$ mg/kg | oral route | 280 | 700 | 750 | 200 | 250 | 250 | 750 | 750 |
| | intravenous route | 30 | 55 | — | 18 | insoluble | 50 | insoluble | 100 |

Chronic Toxicity

The compound of Example 1 was administered orally to young adult rats of Sprague Dawley (Charles River) strain, at dosages of 25, 75 and 150 mg/kg during 3 months.

No anomaly was detected on hematologic examination, on biochemical blood tests and on urinalysis. No change of weight of the organs was found on autopsy.

No histological anomaly, and particularly no liver, kidney or brain injury was found on anatomicopathological examination.

The compound of Example 1 was also administered intravenously to young male adult mice, at dosages of 1 and 5 mg/kg during 1 month.

No substantial modifications were found on hematological examination. The data pertaining to glycemia and serum transaminase level were comparable in the treated animals and in the control animals. No histological anomaly was found on autopsy, particularly no cytologic injury of the liver, the kidneys, the pancreas, the heart or the brain. In addition, the injections were well tolerated locally.

Pharmacological Investigation

I. All the compounds of the formula (I) have a corrective activity on a variety of disorders of the cardiac rhythm, altough to various extents, depending on the individual compounds.

By the intravenous and oral routes, the compounds of the formula (I) have a substantial preventive and curative activity, particularly in the conventional tests concerning arrhythmia induced in animal pharmacology.

a. Two Examples are given to show the preventive action, by the intravenous route:
  1. in guinea-pits, on arrhythmia induced by Strophantine alone or in combination with adrenaline;
  2. in rats, on aconitine-induced rhythm disorders.

The onset of such disorders is delayed by the compounds of the formula (I), at the following dosages (see Table III next page).

b. An Example is given to show the curative activity by the oral route.

The compound of Example 1 corrects the disorders of the cardiac rhythm in non-anesthetized dogs 24 hours after coronary ligation (method according to Harris). As is apparent from following Table IV, the effect is a function of the disage administered.

TABLE IV

| Compound of Example I dose (mg/kg) by the oral route | Number of tests | Percent sinus rhythm θ | |
|---|---|---|---|
| | | Prior to administration of the compound (24 hrs after ligation) | After administration of the compound |
| 10 | 3 | 5% (0–15%) | 25% (0–65%) |
| 25 | 8 | 5.6% (0–18%) | 59% (5–100%) |
| 50 | 6 | 7.6% (0–20%) | 71.6% (25–100%) |

θ The values in parenthesis are the extreme values expressed as percent sinus rhythum.

TABLE III

| Pharmacological test (perfusion of:) | Preventive dosages of the compounds (mg/kg) | | control tests | Compound of Example n° | | | | | |
|---|---|---|---|---|---|---|---|---|---|
| | | | | 1 | 2 | 5 | 7 | 9 | 11 |
| K-Strophantine (0.15mg/ml ; 0.5ml/mn) | 2.5 | decimal | 2.45±0.22 | — | — | — | 2.85±0.1 | — | — |
| | 5 | minutes | | 3.27±0.4 | — | 3.43±0.51 | — | — | — |
| | 10 | ±SD | | 3.18±0.33 | 3.04±0.52 | — | — | — | — |
| K-Strophantine (0.15mg/ml ; 0.5ml/mn) + Adrenaline (5μg/ml ; 0.5ml/mn) | 2.5 | decimal | | — | — | — | 1.74±0.16 | 1.77±0.08 | — |
| | 5 | minutes | 1.21±0.33 | — | — | 1.60±0.35 | — | — | — |
| | 10 | ±SD | | 1.62±0.42 | 2.73±0.5 | | | | 1.3±0.3 |
| Aconitine (50mg/l ; 0.2ml/mn) | 2.5 | seconds | | — | — | — | 185±48 | — | — |
| | 5 | | 85±15 | 141±28 | — | 119±15.5 | — | — | — |
| | 10 | ±SD | | 126±23 | 155±32 | — | — | — | — |
| | 20 | | | — | — | — | — | — | 129±21 |

The various compounds of the above Table are administered just prior to perfusion of the arrhythmogenic materials (K-Strophantine, K-Strophantine-Adrenaline, Aconitine). The values represent the period of time ± SD (standard deviation) before the first signs of arrhythmia appear.

II. On the other hand, the compounds of the formula (I) exhibit antispasmodic and anesthetic properties.

Following Table V shows the activity of the compounds of the formula (I) as compared to that of Papaverine (on $BaCl_2$-induced contraction of the duodenum), of Xylocaine (conduction anesthesia in guinea-pigs) and of Butacaine (surface anesthesia in rabbits).

TABLE V

| Compound of Example n° | Ratio between the dosage of Papaverine and the dosage of Compound (1) producing the same antispasmodic activity | Ratio between the activity of compound (I) and the activity of Butacaine for surface anesthesia, on administration of a same dosage | Ratio between the activity of compound (I) and the activity of Xylocaine for conduction anesthesia, on administration of a same dosage |
|---|---|---|---|
| 1 | 1.5 | 1.5 | 1 |
| 2 | 1 | 1 | 1.4 |
| 4 | 0.8 | 1.4 | 1.5 |
| 5 | 3 | 1.7 | 1.7 |
| 8 | 2.5 | 1.5 | 1 |
| 9 | 4 | 1.65 | 1.6 |
| 11 | 0.2 | 1.5 | 1 |
| 12 | 0.8 | 1 | 1.65 |
| Papaverine | 1 | — | — |
| Butacaine | — | 1 | — |
| Xylocaine | — | — | 1 |

Clinical Tests

Oral administration of the compound of the Example 1 at dosages of 200, 400 and 600 1 mg was found to produce beneficial effects in patients suffering from disorders of the cardiac rhythm. Tolerance was found to be good at such dosages.

The compounds of the formula (I) may be used for the treatment and/or the prevention of disorders of the cardiac rhythm in Man:

Atrial arrhythmia: auricular and junctional extrasystoles; paroxysmal tachycardia; complete arrhythmia.

Ventricular arrhythmia: ventricular extrasystoles; ventricular tachycardia.

Side-effects: an extension of atrioventricular conduction time was noted, which extension may be detrimental to patients suffering from auriculo-ventricular block.

Thus, this invention relates also to therapeutic compositions containing, as active ingredient, a compound of the formula (I) or a therapeutically acceptable acid addition salt thereof, in an amount effective for correcting disorders of the cardiac rhythm. Typically in admixture with a pharmaceutically acceptable excipient.

Such compositions may typically be administered orally or parenterally.

For oral administration, the compositions may be formulated as tablets, capsules, coated tablets and the like, which may contain from 100 mg to 1000 mg active ingredient.

For parenteral administration, the compositions may be formulated as injectable solutions in 1–50 ml ampoules containing 5–1000 mg active ingredient.

Examples of therapeutic compositions are given below:

| 1 - Capsule | |
|---|---|
| Compound of Example 1 | 100 mg |
| Colloidal silica | 2 mg |
| Magnesium stearate | 5 mg |
| 2 - Injectable preparation | |
| Compound of Example 1 | 50 mg |
| NaCl | 38 mg |
| Water for injectable preparation, sufficient to make 5 ml | |
| 3 - Tablet | |
| Compound of Example 1 | 200 mg |
| Frosting sugar | 70 mg |
| Lactose | 40 mg |
| Corn starch | 25 mg |
| Magnesium stearate | 5 mg |
| for a 340 mg tablet | |
| 4 - Oral delayed action composition | |
| Compound of Example 1 | 400 mg |
| Methyl cellulose | 40 mg |
| Shellac | 30 mg |
| Methacrylic polymers | 50 mg |
| Talc | 10 mg |
| Sucrose | 80 mg |
| Lactose | 40 mg |
| Magnesium stearate | 10 mg |
| Ethanol, distilled water, acetone | sufficient amount |

In addition, the invention relates also to a process for the treatment and/or prevention of disorders of the cardiac rhythm in Man, comprising administering to a patient in need thereof a therapeutic composition containing an amount, effective for correcting the disorders of the cardiac rhythm, of a compound of the formula (I) or a therapeutically acceptable acid addition salt thereof.

By the oral route, the daily dosage regimen may be from 100 mg to 4000 mg active ingredient.

By the intravenous route, the dosage administrable by direct injection may be from 50 mg to 1000 mg active ingredient per 24 hours. When administered by slow perfusion, the dosage administrable may be from 500 mg to 4000 mg per 24 hours.

Having now described our invention what we claim as new and desire to secure by Letters Patent is:

1. A compound selected from a compound having the formula:

$$Ar\underset{N}{\overset{N}{\underset{\diagdown O\diagup}{\parallel}}}-N(R)-CH_2-CH(OH)-CH_2-N(R_1)(R_2) \quad (I)$$

in which:
Ar is selected from phenyl and phenyl monosubstituted with halogen,
R is selected from hydrogen, $C_{1-4}$ alkyl and $C_{2-4}$ alkenyl,
$R_1$ and $R_2$ are each selected from hydrogen and $C_{1-4}$ alkyl, and a therapeutically acceptable acid addition salt thereof.

2. 5-N-(3-Diethylamino-2-hydroxy-propyl)-N-methylamino-3-phenyl-1,2,4-oxadiazole and a therapeutically acceptable acid addition salt thereof.

3. 5-N-(3-Diethylamino-2-hydroxy-propyl)-amino-3-phenyl-1,2,4-oxadiazole and a therapeutically acceptable acid addition salt thereof.

4. 5-N-(3-Diethylamino-2-hydroxy-propyl)-N-ethyl-amino-3-phenyl-1,2,4-oxadiazole and a therapeutically acceptable acid addition salt thereof.

5. Therapeutic composition, comprising an amount effective for correcting the disorders of the cardiac rhythm, of a compound selected from a compound having the formula:

$$Ar\underset{N}{\overset{N}{\underset{\diagdown O\diagup}{\parallel}}}-N(R)-CH_2-CH(OH)-CH_2-N(R_1)(R_2) \quad (I)$$

in which:
Ar is selected from phenyl and phenyl monosubstituted with halogen,
R is selected from hydrogen, $C_{1-4}$ alkyl and $C_{2-4}$ alkenyl,
$R_1$ and $R_2$ are each selected from hydrogen and $C_{1-4}$ alkyl, and a therapeutically acceptable acid addition salt thereof together with a pharmaceutically acceptable carrier.

6. Therapeutic composition as claimed in claim 5, wherein said active ingredient is selected from 5-N-(3-diethylamino-2-hydroxy-propyl)-N-methylamino-3-phenyl-1,2,4-oxadiazole and a therapeutically acceptable acid addition salt thereof.

7. Therapeutic composition as claimed in claim 5, formulated for oral administration.

8. Therapeutic composition as claimed in claim 7, in unit dosage form, each unit dose containing 100–1000 mg active ingredient.

9. Therapeutic composition as claimed in claim 5, formulated for parenteral administration.

10. Therapeutic composition as claimed in claim 9, in unit dosage form, each unit dose containing 5–1000 mg active ingredient.

11. Process for the treatment and the prevention of disorders of the cardiac rhythm in Man, comprising administering to a patient in need thereof a therapeutic composition containing an amount, effective for correcting the disorders of the cardiac rhythm, of a compound selected from a compound having the formula:

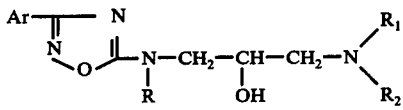

in which:
Ar is selected from phenyl and phenyl monosubstituted with halogen,
R is selected from hydrogen, $C_{1-4}$ alkyl and $C_{2-4}$ alkenyl,
$R_1$ and $R_2$ are each selected from hydrogen and $C_{1-4}$ alkyl, and a therapeutically acceptable acid addition salt thereof.

12. Process as claimed in claim 11, comprising administering orally to said patient 100–4000 mg of a compound selected from the compounds of the formula (I) and a therapeutically acceptable acid addition salt thereof per 24 Hours.

13. Process as claimed in claim 11, comprising administering to said patient, by direct intravenous injection, 50–1000 mg per b 24 hours of a compound selected from the compounds of the formula (I) and a therapeutically acceptable acid addition salt thereof.

14. Process as claimed in claim 11, comprising administering to said patient, by slow perfusion, 500–4000 mg per 24 hours of a compound selected from the compounds of the formula (I) and a therapeutically acceptable acid addition salt thereof.

15. Therapeutic composition as claimed in claim 5, wherein said active ingredient is selected from 5-N-(3-Diethylamino-2-hydroxy-propyl)-amino-b 3-phenyl-1,2,4-oxadiazole and a therapeutically acceptable acid addition salt thereof.

16. Therapeutic composition as claimed in claim 5, wherein said active ingredient is selected from 5-N-(3-Diethylamino-2-hydroxy-propyl)-N-ethyl-amino-3-phenyl-1,2,4-oxadiazole and a therapeutically acceptable acid addition salt thereof.

17. Process as claimed in claim 11, wherein said compound is selected from 5-N-(3-Diethylamino-2-hydroxy-propyl)-N-methylamino-3-phenyl-1,2,4-oxadiazole and a therapeutically acceptable acid addition salt thereof.

18. Process as claimed in claim 11, wherein said compound is selected from 5-N-(3-Diethylamino-2-hydroxy-propyl)-amino-3-phenyl-1,2,4-oxadiazole and a therapeutically acceptable acid addition salt thereof.

19. Process as claimed in claim 11, wherein said compound is selected from 5-N-(3-Diethylamino-2-hydroxy-propyl)-N-ethyl-amino-3-phenyl-1,2,4-oxadiazole and a therapeutically acceptable acid addition salt thereof.

* * * * *